(12) United States Patent
Buerk

(10) Patent No.: US 9,877,638 B2
(45) Date of Patent: Jan. 30, 2018

(54) ENDOSCOPE WITH ADJUSTABLE VIEWING ANGLE

(71) Applicant: Karl Storz SE & Co. KG, Tuttlingen (DE)

(72) Inventor: Andre Buerk, Villingen-Schwenningen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 857 days.

(21) Appl. No.: 13/631,302

(22) Filed: Sep. 28, 2012

(65) Prior Publication Data

US 2013/0085338 A1    Apr. 4, 2013

(30) Foreign Application Priority Data

Sep. 30, 2011    (EP) .................................... 11183386

(51) Int. Cl.
*A61B 1/00*    (2006.01)
*A61B 1/04*    (2006.01)

(52) U.S. Cl.
CPC ...... *A61B 1/00183* (2013.01); *A61B 1/00096* (2013.01); *A61B 1/042* (2013.01)

(58) Field of Classification Search
USPC ................................................ 600/173, 176
See application file for complete search history.

(56) References Cited

U.S. PATENT DOCUMENTS

| 3,913,568 | A | 10/1975 | Carpenter |
| 6,638,216 | B1 * | 10/2003 | Durell .......................... 600/173 |
| 2005/0234296 | A1 | 10/2005 | Saadat et al. |
| 2007/0055103 | A1 * | 3/2007 | Hoefig et al. ................. 600/173 |

FOREIGN PATENT DOCUMENTS

| DE | 2328595 A1 | 1/1974 |
| DE | 19927816 A1 | 1/2001 |
| EP | 1759629 A1 | 3/2007 |
| WO | 0217773 A2 | 3/2002 |

OTHER PUBLICATIONS

European Search Report; Application No. EP 11 18 3386; issued Feb. 3, 2012; dated Feb. 13, 2012; 9 pages.

\* cited by examiner

*Primary Examiner* — Timothy J Neal
(74) *Attorney, Agent, or Firm* — Whitmyer IP Group LLC

(57) ABSTRACT

An endoscope with a viewing angle that can be adjusted within a predetermined angular range includes a movable light-diverting device on the distal end of the endoscope on whose orientation the viewing angle of the endoscope depends, and a jointed device to movably hold the light-diverting device. The jointed device is configured for a movement of the light-diverting device that includes more than only a pivoting about a single pivot axis.

13 Claims, 4 Drawing Sheets

ENDOSCOPE WITH ADJUSTABLE VIEWING ANGLE

FIELD OF THE INVENTION

The present invention relates to an endoscope with a viewing angle that can be adjusted within a predetermined angular range.

BACKGROUND OF THE INVENTION

In addition to endoscopes for medical and non-medical technical applications, whose viewing angle is parallel to the longitudinal axis of the endoscope shaft, endoscopes with other fixed viewing angles have been developed for some time. The viewing angle of an endoscope is understood here and hereinafter always to mean the direction facing from the distal end of the endoscope, in which an object is situated that appears in the center of the image recorded by means of the endoscope. In many applications, however, a fixed viewing angle is a disadvantage. In the worst case, for example during a medical procedure, the endoscope must be replaced numerous times. In such cases it is an advantage to use an endoscope with a viewing angle that can be selected or adjusted in situ.

To select or adjust the viewing angle, the distal end of the endoscope can comprise a movable light-diverting device on whose orientation the viewing angle of the endoscope is dependent. The light-diverting device includes, for example, a prism or mirror, whose orientation determines in which direction (with respect to the distal end of the endoscope) observed objects are situated, or from which direction light falling onto the distal end of the endoscope is switched into an observation beam path and/or is diverted onto a light-sensitive image sensor.

In constructing an endoscope with adjustable viewing angle, a whole range of requirements must be taken into account. In particular, to achieve a high light intensity, a light-diverting device with the greatest possible cross-section is desired. In addition, it is desirable to have the greatest possible angular range within which the viewing angle can be adjusted. At the same time, the distal end of an endoscope always has only a limited structural space available for the light-diverting device and its mobility. With increasing miniaturization or decreasing shaft cross-section, the available structural space becomes constantly smaller. Therefore new approaches are required in order to comply more closely with the requirements for constructing an endoscope.

SUMMARY OF THE INVENTION

It is an object of the present invention to provide an improved endoscope with a viewing angle that can be adjusted within a predetermined angular range.

This object is achieved by means of an endoscope with a viewing angle that can be adjusted within a predetermined angular range.

Refinements are also indicated herein.

An endoscope with a viewing angle that is adjustable within a predetermined angular range includes a movable light-diverting device on the distal end of the endoscope, on whose orientation the viewing angle of the endoscope depends, and a jointed device for movably securing the light-diverting device, such that the jointed device is configured for a mobility of the light-diverting device that includes more than just a capacity to pivot about a single pivot axis.

The viewing angle of the endoscope is the direction—with respect to the distal end of the endoscope—in which an object is situated that appears in the center of an image captured by means of the endoscope. The light-diverting device includes, in particular, a prism, an object lens, a lens or a mirror, and defines by its orientation or its angular position the viewing angle of the endoscope. In addition, the viewing angle can be influenced by a translational movement of the light-diverting device.

The mobility of the light-diverting device includes, for example, a series of pivot movements about different pivot axes. In this case the light-diverting device always pivots about only one pivot axis, or partly or always simultaneously about several pivot axes that, in particular, are parallel to one another. Alternatively, the mobility of the light-diverting device can include a superimposition of a pivot movement with a translational movement along a straight or curved path. Here the pivot movement and the translational movement can be in a constant ratio or in a ratio that changes during the movement in predetermined manner.

The light-diverting device can be configured to cause, during pivoting of the light-diverting device at a determined angle, a pivoting of the viewing direction at the same angle. For example, the light-diverting device can be an object lens or lens with which a light-sensitive image sensor is rigidly connected; said sensor is disposed in the image plane of the object lens or lens and can move with the light-diverting device. Alternatively the light-diverting device can be configured to cause, during pivoting of the light-diverting device at an angle, a pivoting of the viewing direction at twice that angle. An example is a mirror or prism with a reflecting surface that diverts light from observed objects directly or indirectly to a video camera or light-sensitive image sensor or to an eyepiece.

A light-sensitive image sensor can be disposed at the distal end of the endoscope directly downstream in the light path from the light-diverting device or from an object lens positioned downstream in the light path from the light-diverting device. The endoscope can include an arrangement of rod lenses or an arranged bundle of light conductors in order to conduct the light diverted by the light-diverting device to an eyepiece, to a light-sensitive image sensor or to a video camera at the proximal end of the endoscope.

A jointed device, which is configured for mobility of the light-diverting device that includes more than just a capacity to pivot about a single pivot axis, can with a given structural space allow a larger light-diverting device, in particular a greater cross-section of the light-diverting device, in particular greater length and/or height of a prism. Thus, for example, a greater angular range of possible viewing angles and/or a greater light intensity can become possible. In particular, a jointed device that is configured for a mobility of the light-diverting device that encompasses more than only a pivoting about a single pivot axis, can make possible an optimal position of the light-diverting device with several viewing directions of the endoscope with respect to the structural space required for the light-diverting device and with respect to the arrangement of the light-diverting device within the observation beam path.

With an endoscope as described here, the jointed device includes in particular a first joint that defines a first pivot axis, and a second joint that defines a second pivot axis.

The first pivot axis and the second pivot axis are different from one another and in particular parallel and in particular perpendicular to the longitudinal axis of the endoscope and to the adjustable viewing angles. The jointed device can be configured for simultaneous or alternating pivoting about the first pivot axis and the second pivot axis. Joints that each make possible a pivoting about an associated pivot axis can be configured in particular with low play and friction and thus can allow a precise movement of the light-diverting device.

In particular, the first joint is configured and disposed to allow a pivoting movement of the light-diverting device about the first pivot axis if the viewing angle is situated within a first partial area of the predetermined angular range, and the second joint is configured and disposed to allow a pivoting movement of the light-diverting device about the second pivot axis if the viewing angle is situated within a second partial area of the predetermined angular range.

In particular, the jointed device is configured to allow a pivot motion of the light-diverting device about the first pivot axis only when the viewing angle is situated in the first partial area, and/or to allow a pivot movement of the light-diverting device about the second pivot axis only when the viewing angle is situated in the second partial area.

In particular, the first partial area and second partial area border on one another.

The first partial area and the second partial area border on one another in that the upper border of the first partial area corresponds to the lower border of the second partial area, or vice versa. The two partial areas, in particular, thus have—apart from mechanical play—no overlap.

An endoscope with two pivot axes as described here also includes in particular a device to hamper a pivot movement about the first pivot axis, such that the hampering device is configured to hamper the pivot movement at least when the viewing angle is situated outside the first partial area.

A hampering device can be configured to hamper the pivot movement about the first pivot axis within the entire predetermined angular range or only within a portion of the predetermined angular range, in particular only outside the first partial area. Hampering of the pivot movement about the first pivot axis can cause the light-diverting device preferably to pivot about the second pivot axis if this is possible. Automatic selection of the pivot axis can thereby occur in simple manner.

An endoscope with two pivot axes as described here can also include a device to block a pivot movement about the second pivot axis, such that the blocking device is configured to block the pivot movement about the second pivot axis if the viewing angle is not situated within the second partial area.

The blocking device includes, for example, a bolt, which engages in a predetermined angular position in such a way that a pivot movement about the second pivot axis is blocked. In particular, together with a device to hamper a pivot movement about the first pivot axis as described above, the blocking device can make possible an automatic or self-actuating selection of the pivot axis depending on the viewing angle.

An endoscope with two pivot axes as described here, in addition, can include an elastic element that is coupled with the jointed device in such a way that at least either the first joint is pre-tensed in the direction toward a first predetermined angular position or the second joint is pre-tensed in the direction toward a second predetermined angular position.

The elastic element includes, for example, a flat spring, a spiral spring or a component made of an elastomer. In particular, the first joint and/or the second joint are pre-tensed in the direction toward the angular positions that they assume at the boundary between the partial areas of the predetermined angular ranges. A pre-tensing of the first joint and/or of the second joint can make possible in simple manner a self-actuating selection of the pivot axis depending on the selected viewing angle of the endoscope.

In an endoscope with two pivot axes as described here, the jointed device can include a first diverter, which connects the first joint and the second joint, and a second diverter, which connects a third and a fourth joints, such that the second joint and the fourth joint are mechanically rigidly connected with the light-diverting device.

To make possible a movement of the light-diverting device that constitutes more than only a parallel sliding along a curved path, the first joint, the second joint, the third joint and the fourth joint are not disposed in a parallelogram. For this purpose, in particular, the distance of the first joint and the third joint and the distance of the second joint and the fourth joint are different and/or the length of the first diverter or the distance of the first joint and of the second joint on the one hand and the length of the second diverter or the distance of the third joint and the fourth joint on the other hand are different.

In an at least partially symmetrical arrangement of the jointed device at two opposite sides of the light-diverting device, which is advantageous in particular with respect to mechanical robustness, two parallel first diverters are disposed in each case at opposite sides of the light-diverting device and/or two parallel second diverters at opposite sides of the light-diverting device.

Use of two diverters that are not of equal length and/or not parallel can, with appropriate configuration, make possible a movement of the light-diverting device that consists of a superimposition, dependent on the viewing angle, of a pivot movement and of a translational movement. This movement can make possible an arrangement of the light-diverting device with several viewing angles, in particular with extreme viewing angles at the edge of the predetermined angular range, an arrangement that is optimal with respect to the required structural space and with respect to the observation beam path.

In an endoscope as described here, the jointed device can include a gliding surface device for guidance along a path.

The gliding surface device can be configured for guidance along a straight or a curved path. The jointed device can include several gliding surface devices for guidance along a straight or curved path in each case, such that, for example, the proximal end and the distal end of a prism are guided by one associated gliding surface device each.

In addition, the jointed device can include a joint for pivoting about an axis and a gliding surface device for guidance along a path. In particular, the joint and the linear guidance are disposed in such a way that the linear guidance makes possible a motion of the joint and of the light-diverting device along the path predetermined by the linear guidance. Alternatively, the joint and the linear guidance can be disposed in such a way that the joint makes possible a pivoting of the linear guidance, of the path defined by the linear guidance, and of the light-diverting device about a pivot axis defined by the joint.

A gliding surface device with gliding surfaces of almost unlimited shapability can make possible a movement of the light-diverting device that is of almost unlimited complexity. Thus, under some circumstances, for every adjustable viewing angle of the endoscope an optimal arrangement and alignment or orientation of the light-diverting device can be achieved.

In an endoscope in which the jointed device includes a gliding surface device and a joint, the jointed device can also include a coupling device that couples a pivoting about the pivot axis defined by the joint and a movement along the path defined by the linear guidance with one another.

The coupling device includes in particular one or more diverters, a sliding block guide, a cam control, one or more toothed wheels or a combination of these. The coupling device can make it possible that despite several degrees of freedom of the light-diverting device, only a control wire, a user interface, a motor or other control device is required in order to make possible a predetermined movement of the light-diverting device.

In an endoscope as described here, the jointed device can also include at least either a sliding block guide or a diverter or cam control or an elastic element.

In all endoscopes described here, it is possible, for example, to provide on the proximal end several control wires and/or several motors or a toothed wheel drive or other drive or other coupling device, in order to control degrees of freedom provided by means of the jointed device, independently of one another or synchronized.

In an endoscope as described here, the light-diverting device can include at least either a prism, an object lens, a lens or a mirror.

An endoscope as described here can also include a light-sensitive image sensor, which is coupled with the light-diverting device in such a way that it can move with the light-diverting device.

The light-sensitive image sensor can be mechanically rigidly connected with the light-diverting device. Alternatively, the light-sensitive image sensor can be coupled with the light-diverting device in such a way that it can move synchronously with it, but can, for example, slide along another path or pivot about another axis.

BRIEF DESCRIPTION OF THE DRAWINGS

Hereinafter, embodiments are described in greater detail with reference to the appended drawings, which are as follows.

DETAILED DESCRIPTION OF THE INVENTION

Figure 1:
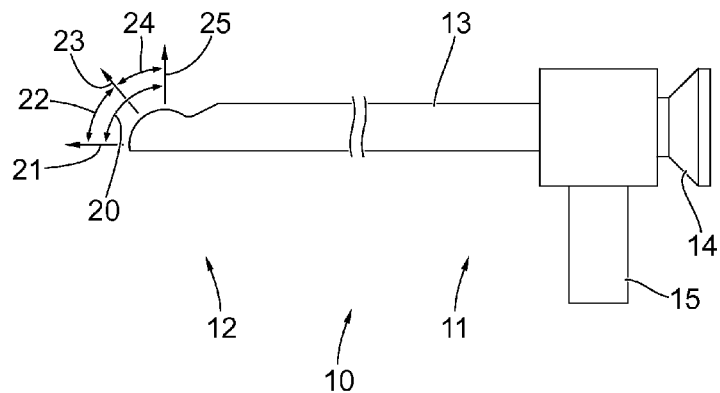
FIG. 1 shows a schematic depiction of an endoscope with an adjustable viewing angle.

FIG. 1 shows a schematic depiction of an endoscope 10 with a proximal end 11 and a distal end 12. The endoscope 10 comprises a shaft 13, which extends from the proximal end 11 to the distal end 12. The shaft 13 in each case can be partly or completely rigid or flexible, straight or curved. At the proximal end 11 the endoscope 10 comprises an eyepiece 14 for direct visual observation by the human eye and/or a coupling for a video camera. In addition, the endoscope 10 comprises at the proximal end 11 a coupling 15 for coupling the endoscope 10 with an external light source by means of a light-diverting cable.

At the distal end 12 a movable light-diverting device, not shown in FIG. 1, is provided that makes possible, in particular, a continuously adjustable viewing angle 21, 23, 25. Situated between extreme viewing angles 21, 25 is an angular range 20 within which the viewing angle can be adjusted. FIG. 1 indicates two partial areas 22, 24 of the angular range 20; they are referred to in the embodiment that is presented below with reference to FIGS. 4 through 6. The first of these partial areas 22 extends from a first viewing angle 21 essentially parallel to the longitudinal axis of the shaft 13 to a second viewing angle 23. The second partial area 24 extends from the second viewing angle 23 to a third viewing angle 25.

FIGS. 2 through 8 show schematic depictions of embodiments of the distal end 12 of the endoscope 10 from FIG. 1. The depictions in FIGS. 2 through 8 have the character of sectional depictions insofar as they show the interior of the shaft 13 at the distal end 12 of the endoscope 10. The planes of projection of FIGS. 2 through 8 are parallel to the plane of projection of FIG. 1, to the longitudinal axis of the shaft 13 and to the adjustable viewing angles 21, 23, 25 of the endoscope 10.

The structure of the shaft 13 of the endoscope 10, in particular the structure of its wall and/or walls, is not shown in FIGS. 2 through 8. FIGS. 2 through 8 each indicate a distal lens 17 and a window component 18, which restrict the structural space available for a movable light-diverting device 30. Light from an object entering through the window component 18 into the distal end 12 of the endoscope 10 can be diverted to the distal lens 17 by the light-diverting device 30. A rod lens system or a light-sensitive image sensor can be positioned downstream in the light path from the lens 17. The window component 18, light-diverting device 30 and distal lens 17 indicate the observation beam path of the endoscope 10.

In the embodiments illustrated in FIGS. 2 through 8, the light-diverting device 30 is a prism with a light inlet side facing the window component 18, a light outlet side facing the distal lens 17, and a reflecting, especially totally reflecting level surface, which extends from the light inlet side to the light outlet side.

Figure 2:
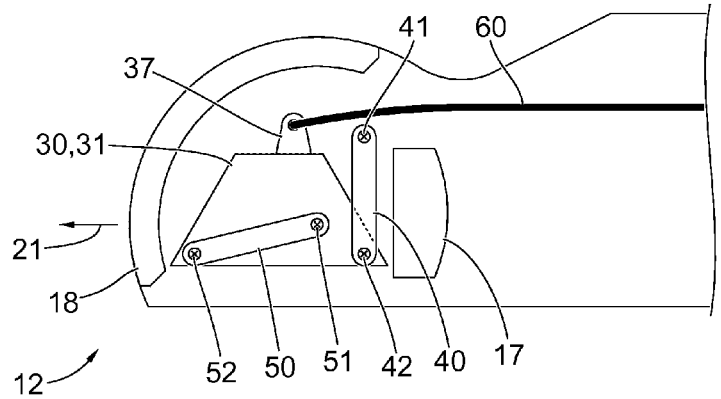
FIG. 2 shows a schematic depiction of a distal end of an endoscope.
Figure 3:
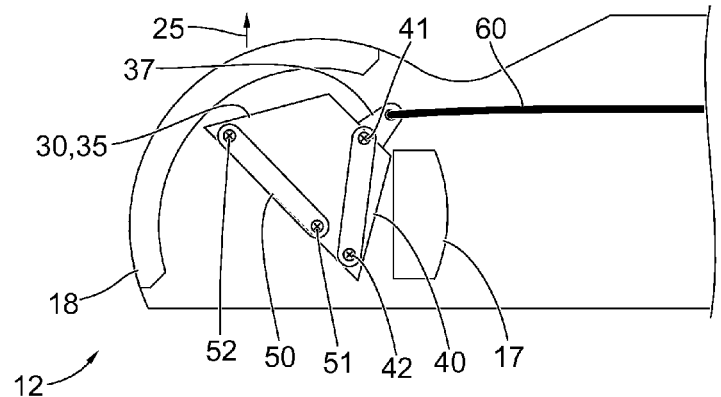
FIG. 3 shows another schematic depiction of the distal end from FIG. 2.

FIGS. 2 and 3 show schematic depictions of an embodiment of a distal end 12 of an endoscope, in which the prism 30 is mounted in the endoscope so that it is movable by means of a jointed device consisting of a first diverter 40 and a second diverter 50. Parallel to the diverters 40, 50, additional diverters can be disposed on an opposite side of the prism 30 that is turned away from the observer. The first diverter 40 is jointedly connected by a first joint 41 with the shaft 13 of the endoscope 10 and by a second joint 42 with the prism 30. The second diverter 50 is connected by a third joint 51 with the shaft 13 and by a fourth joint 52 with the prism 30. The first joint 41 and the third joint 51 are anchored immovably in the shaft 13 of the endoscope. The second joint 42 and fourth joint 52 are directly or indirectly fastened on sites at a distance from one another on the prism 30. The first joint 41, second joint 42, third joint 51 and fourth joint 52 each define—possibly together with corresponding additional joints of parallel diverters that are not shown in FIGS. 2 and 3—a pivot axis perpendicular to the planes of projection of FIGS. 2 and 3.

FIGS. 2 and 3 show the prism in two different positions 31, 35, which correspond to the first viewing angle 21 or to the third viewing angle 25 or are associated with them (compare FIG. 1). To move or mechanically control the prism 30, a control wire 60 is provided, whose distal end is jointedly connected with a control lever 37 on the prism 30. The control wire 60 extends, in particular, from the proximal end 11 to the distal end 12 of the endoscope 10 (compare FIG. 1). At the proximal end 11 of the endoscope, the control wire 60 is coupled in particular with a slide bar, a rotary wheel or other user interface, on which the medical staff can select the viewing angle of the endoscope 10. Alternatively, the control wire 60 can be coupled at the proximal end 11 of the endoscope 10 with a motor for motorized switching of the viewing angle.

In the embodiment in FIGS. 2 and 3 the pivot axis defined by the third joint 51 is disposed as close as possible to the curvature center point of the inner surface of the window component 18. The pivot axis of the second diverter 50, defined by the fourth joint 52, is as close as possible to the point of the prism 30 that is closest to the window component 18. The first diverter 40, first joint 41 and second joint 42 are configured and disposed in such a way that the side of the prism 30 facing the distal lens 17 is positioned over the greatest possible pivot range as optimally as possible in relation to the distal lens 17. Owing to the arrangement and configuration of the diverters 40, 50 and joints 41, 42, 51, 52, contrary to the depictions in FIGS. 2 and 3, the movement of the prism 30 can be adjusted within broad boundaries to the observation beam path, the optical properties of the prism 30 and the structural space available for it.

Figure 4:
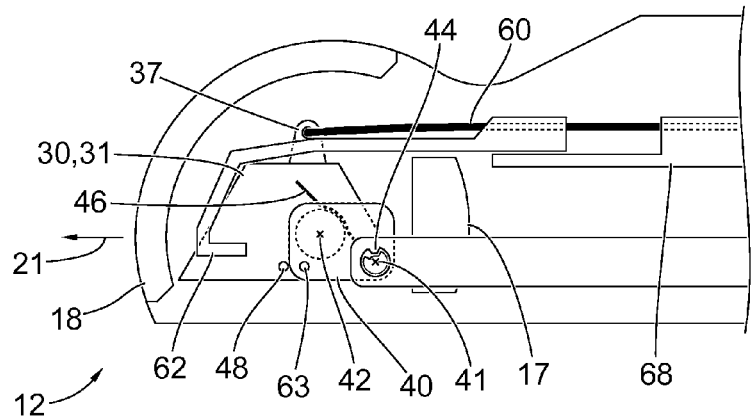
FIG. 4 shows a schematic depiction of a distal end of an endoscope.
Figure 5:
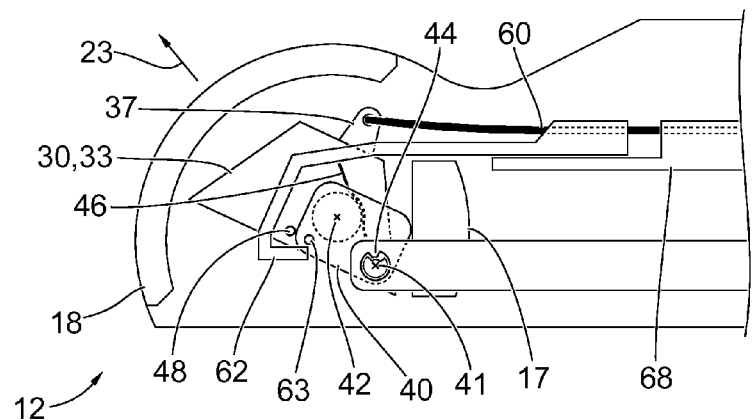
FIG. 5 shows another schematic depiction of the distal end from FIG. 4.
Figure 6:
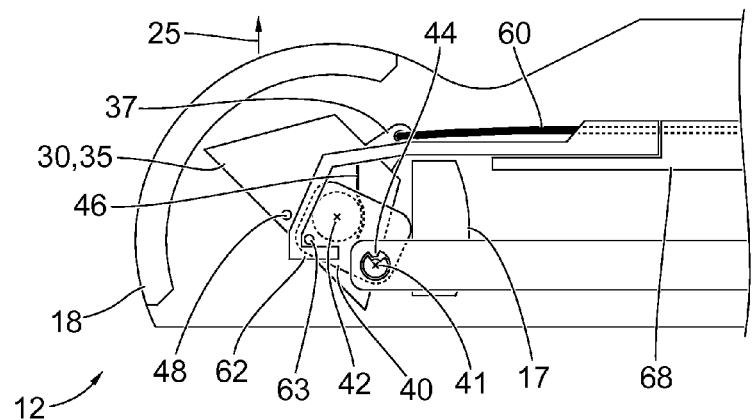
FIG. 6 shows another schematic depiction of the distal end from FIGS. 4 and 5.

FIGS. 4 through 6 show an embodiment of a distal end 12 of an endoscope that resembles in some features the embodiment in FIGS. 2 and 3, in particular in the configuration of the light-diverting device 30 as a prism, the limiting of the structural space available for the prism 30 owing to a distal lens 17 and a window component 18 as well as in the mechanical control of the prism 30 by means of a control wire 60 whose distal end is jointedly coupled with a control lever 37 on the prism 30.

In the embodiment in FIGS. 4 through 6, the prism 30 is mounted by means of a diverter 40 in the shaft 13 of the endoscope. The diverter 40 is depicted in the embodiment in FIGS. 4 through 6 as a rectangular plate with rounded corners and essentially parallel to the planes of projection of FIGS. 4 through 6. The diverter 40 is connected by a first joint 41 with the endoscope or its shaft 13 and by a second joint 42 with the prism 30. The pivot axes defined by the first joint 41 or the second joint 42 are parallel to one another and perpendicular to the planes of projection of FIGS. 4 through 6. Parallel to the diverter 40, an additional diverter, not shown in FIGS. 4 through 6, can be provided on a side of the prism 30 that is turned away from the observer.

On the first joint 41, a protrusion 44 on the fixed portion of the joint 41 is provided that engages in the radial direction in a recess in an axis pin on the diverter 40, such that the protrusion 44 is smaller in the peripheral direction than the recess. Thereby the protrusion 44 restricts the pivot movement of the diverter 40 to a pivoting movement between the two angular positions shown in FIGS. 4 and 5. Alternatively, contrary to the depiction in FIGS. 4 through 6, a mechanical stop, restricting the pivot movement of the diverter 40, can be provided at another site.

The axle or the axis pin on the diverter 40, which defines the second joint 42, has a greater diameter than the first joint 41. In addition, a flat spring 46 is provided that is affixed directly or indirectly on the prism 30 and is contiguous with the axle or axle pin on the diverter 40. The greater diameter of the second joint 42 and the flat spring 46 cause markedly greater friction to occur in the second joint 42 than in the first joint 41.

On the prism 30, or connected with the prism 30, a stop 48 is provided that extends from the prism 30 in the direction perpendicular to the planes of projection of FIGS. 4 and 5, at least partly into the plane in which the diverter 40 is situated. With the prism in the positions 31, 33 shown in FIGS. 4 and 5, the stop 48 is contiguous with the diverter 40. Thereby the stop 48 restricts a pivot movement of the prism 30 in relation to the diverter 40 in the mathematically positive rotary direction or in counterclockwise direction (with respect to the depictions in FIGS. 4 and 5). Thereby the stop 48 prevents, in particular, a movement of the prism 30 beyond the position 31 in the mathematically positive sense or in counterclockwise direction and thus also a viewing angle that (starting from the third viewing angle 25 and the second viewing angle 23) extends beyond the first viewing angle 21.

The stop 48, however, makes possible a rotary movement of the prism 30 from the position 33 shown in FIGS. 4 and 5 in the mathematically negative rotary direction or clockwise to the position 35 shown in FIG. 6. With the prism 30 in position 35, the stop 48 is not contiguous with the diverter 40.

In addition, in the embodiment in FIGS. 4 through 6, a gate valve 62 and a tooth element 63 are provided. The tooth element 63 has, in particular, the shape of a rod or of a glide surface that extends in the direction perpendicular to the planes of projection of FIGS. 4 through 6. The gate valve 62 is mechanically coupled with the control wire 60, in particular by soldering, cementing or other type of joining. For precise guidance of the gate valve 62 along a predetermined straight path and optionally, in addition, for guidance of the control wire in its area proximally from the gate valve 62, a linear guidance 68 is provided.

In FIG. 4 the prism 30 is shown in a first position 31, which corresponds to the first viewing direction 21 indicated in FIG. 1. The prism 30 is shown in FIG. 5 in a second position 33, which corresponds to the second viewing angle 23. In FIG. 6 the prism 30 is shown in a third position 35, which corresponds to the third viewing angle 25. Thus the proximal end or the proximal front surface of the gate valve 62 simultaneously strikes a corresponding surface on the linear guidance 68 in order to prevent an additional movement of the control wire 60 and gate valve 62 in the proximal direction.

In the area from the first viewing angle 21 or the first position 31 of the prism 30 to the second viewing angle 23 or the second position 33 of the prism 30, the movement of the prism 30, without a relative movement of the prism 30 and diverter 40, is possible only by a pivoting of the diverter 40 together with the prism 30 about the pivot axis defined by the first joint 41. As mentioned, the first joint 41 is configured with the protrusion 44 in order to restrict the pivot movement of the diverter 40 to the area between the positions shown in FIGS. 4 and 5 or to the area between the first viewing angle 21 and the second viewing angle 23. Because, as mentioned, friction in the second joint 42 is greater than in the first joint 41, in the area between the first viewing angle 21 and the second viewing angle 23, no relative movement of the prism 30 and diverter 40 occurs.

In the area between the second viewing angle 23 or the second position 33 of the prism 30 and the third viewing angle 25 or the third position 35 of the prism 30, the gate valve 62 and the tooth element 63 are mechanically engaged or in a form-locked connection. The restriction of the pivot range of the diverter 40 by the protrusion 44 on the first joint 41 on the one hand and the form-lock between the gate valve 62 and the tooth element 63 on the other hand, in the area between the second viewing angle 23 or second position 33 of the prism 30 and the third viewing angle 25 or third position 35 of the prism 30, hold the diverter 40 in the position shown in FIGS. 5 and 6. In this area, the prism 30 thus pivots exclusively about the pivot axis defined by the second joint 42.

Instead of the protrusion 44 on the first joint 41 to restrict movement in the first joint 41 and instead of the stop 48 to restrict movement in the second joint 42, other mechanical devices can be foreseen that restrict the pivot range of the diverter 40 in relation to the distal end 12 of the endoscope 10 or the pivot range of the prism 30 in relation to the diverter 40.

Altogether, the angular range 20 of viewing angles 21, 23, 25 (see FIG. 1) thus breaks down into a first partial area 22 and a second partial area 24 because of the restriction of pivot movement on the first joint 41, the different friction in the first joint 41 and in the second joint 42, and the engagement, depending on the position of the control wire 60, between the gate valve 62 and the tooth element 63. In the first partial area 22 between the first viewing angle 21 and the second viewing angle 23, the prism 30 pivots exclusively about the pivot axis defined by the first joint 41, and the stop 48 is contiguous with the diverter 40. In the second partial area 24 between the second viewing angle 23 and the third viewing angle 25, the prism 30 pivots exclusively about the pivot axis defined by the second joint 42.

Similar results can be obtained without gate valve 62, tooth element 63 and different friction in the joints 41, 42, for example in that the diverter 40 is pre-tensed in the position shown in FIGS. 5 and 6 by means of a spring or elastic element, and/or in that the prism 30 and the diverter 40 are pre-tensed in the relative position shown in FIGS. 4 and 5 by a spring or other elastic element.

Figure 7:
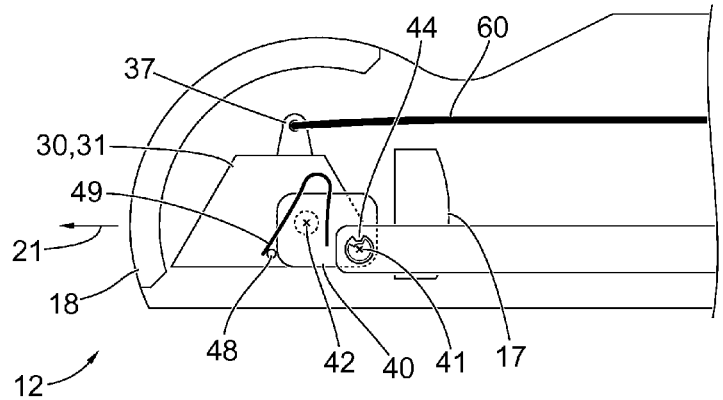
FIG. 7 shows a schematic depiction of a distal end of an endoscope.
Figure 8:
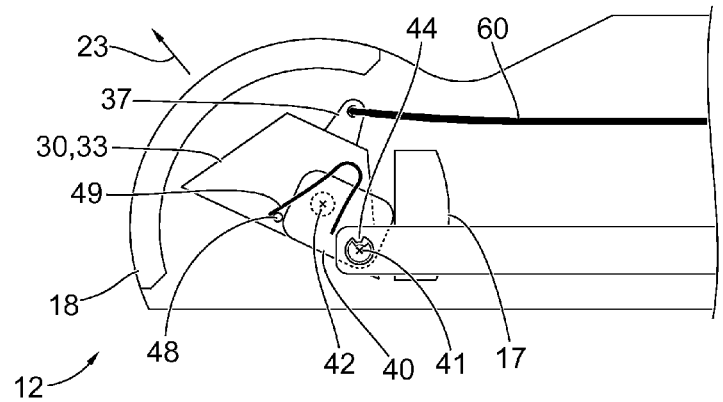
FIG. 8 shows another schematic depiction of the distal end from FIG. 7.
Figure 9:
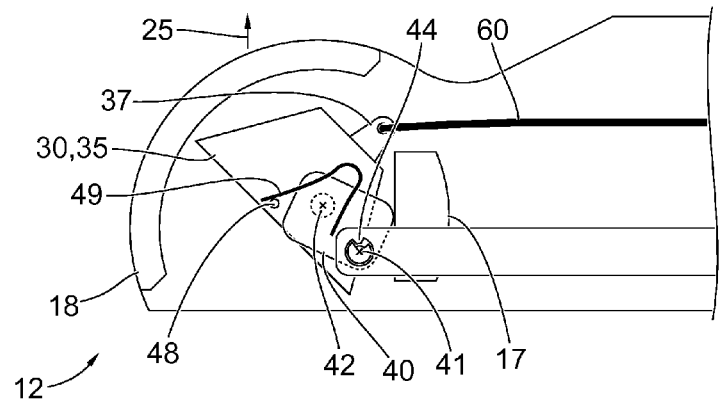
FIG. 9 shows another schematic depiction of the distal end from FIGS. 7 and 8.

FIGS. 7 through 9 show an embodiment of a distal end 12 of an endoscope that in some features resembles the embodiment in FIGS. 4 through 6, particularly in the configuration of the light-diverting device 30 as a prism, in the restriction of the structural space available for the prism 30 owing to a distal lens 17 and a window component 18, in the mounting of the prism 30 by means of a diverter 40 in the shaft 13 of the endoscope, as well as in the mechanical control of the prism 30 by means of a control wire 60 whose distal end is coupled jointedly with a control lever 37 on the prism 30.

Contrary to the embodiment in FIGS. 4 through 6, the embodiment in FIGS. 7 through 9 foresees a flat spring 49 one end of which (the one to the right in FIGS. 7 through 9) is rigidly connected with the diverter 40 and the other end of which (to the left in FIGS. 7 through 9) is contiguous with the stop 48. The flat spring 49 presses the stop 48 flexibly against the diverter 40. Thereby the flat spring 49 pre-tenses the prism 30 in the direction toward the position shown in FIGS. 7 and 8 in relation to the diverter 40.

The flat spring 49 has the effect that, starting from the first viewing angle 21 shown in FIG. 7 and the first position 31 of the prism 30, upon movement of the control wire 60 in the proximal direction, the stop 48 first remains contiguous with the diverter 40 and the prism 30 together with the diverter 40 is pivoted about the pivot axis defined by the first joint 41. In the second viewing angle 23 shown in FIG. 8 and the second position 33 of the prism 30, the diverter 40 has attained its maximum deflection as defined by the protrusion 44 on the first joint 41. If the control wire 60 is drawn farther in the proximal direction, the prism 30 must therefore be pivoted in relation to the diverter 40, so that the stop 48 is withdrawn by the diverter 40. Therefore the movement of the prism 30 from the second position 33 to the third position 35 shown in FIG. 9 occurs against the elastic force of the flat spring 49.

If, starting from the third position 35 of the prism 30 shown in FIG. 9, the control wire 60 is moved in the distal direction, the flat spring 49 presses the stop 48 toward the diverter 40. Therefore, a pivot movement of the prism 30 first occurs in relation to the diverter 40 about the pivot axis defined by the second joint 42, such that the diverter 40 remains unmoved. Not until the second position 33 of the prism 30 as shown in FIG. 8 is the stop 48 contiguous with the diverter 40. An additional movement of the prism 30 in relation to the diverter 40 is no longer possible at this point. Therefore, in a further movement of the control wire 60 in the distal direction, the prism 30 together with the diverter 40 pivots about the pivot axis defined by the first joint 41.

In the embodiment presented with reference to FIGS. 7 through 9, a few features of the embodiment from FIGS. 4 through 6 can be dispensed with, in particular the gate valve 62, the flat spring 46 on the second joint 42, and the enlarged diameter on the second joint 42.

In the embodiment presented with reference to FIGS. 7 through 9, instead of the flat spring 49 another elastic element can be foreseen that pre-tenses the prism 30 into the position shown in FIGS. 7 and 8 in relation to the diverter 40. Alternatively or in addition, another flat spring or another elastic element can be foreseen that pre-tenses the diverter in the direction toward the position shown in FIGS. 8 and 9 in relation to the distal end 12 of the endoscope. In addition, alternatively, a single elastic element can be foreseen, which both pre-tenses the prism 30 in the direction toward the position shown in FIGS. 7 and 8 in relation to the diverter 40 and pre-tenses the diverter 40 in the direction toward the position shown in FIGS. 8 and 9 in relation to the distal end 12 of the endoscope.

Instead of the measures presented above with reference to FIGS. 4 through 9 to determine in which angular ranges the prism is pivoted about the pivot axes defined by the joints 41, 42, or in addition to them, other measures are also possible. For example, on the gate valve 62 and on the diverter 40 on surface areas that are parallel to one another and touch one another, straight or curved fine furrows or other textures can be foreseen in order to support the pivot movement of the diverter 40 through the linear movement of the gate valve 62.

In addition, friction linings can be foreseen at this or other sites. For example, friction linings can be foreseen on a surface on the first joint 41 parallel to the planes of projection of FIGS. 4 through 9 and on an element that can be linearly displaced with the gate valve 62. These friction linings can be disposed and configured in such a way that they are in engagement only in a predetermined angular range, in particular only in the range between the second position 33 and the third position 35 of the prism and hamper pivoting of the diverter 40 about the pivot axis defined by the first joint 41.

Alternatively or in addition to friction linings and/or form-locked control by means of one or more control valves, magnets can be used to promote or to hamper pivot movement about a pivot axis. Magnets can also be usable instead of springs or other elastic elements. Hampering is also possible by means of one or more piezo elements.

To operate the prism 30, instead of the control wire or in addition to it, additional or other means can be foreseen. For example, the diverter 40 can be moved independently of the prism 30 by means of an additional power wire. Two diverters 40 disposed on opposite sides of the prism 30 parallel to one another can be moved by means of two control wires. Each two, three or more control wires are, in particular, coupled with one another at the proximal end 11 of the endoscope 10.

Instead of one or more control wires, it is possible to provide one or more electric-powered, magnetic, pneumatic, hydraulic, piezo motor or other power drives. In addition, it is possible to use power drives along with bimetallic springs or other arrangements that change shape on the basis of different thermal expansion coefficients depending on temperature. Moreover, use can be made of power drives using shape memory alloys, which employ shape changes by means of a temperature-dependent lattice transformation.

Figure 10:
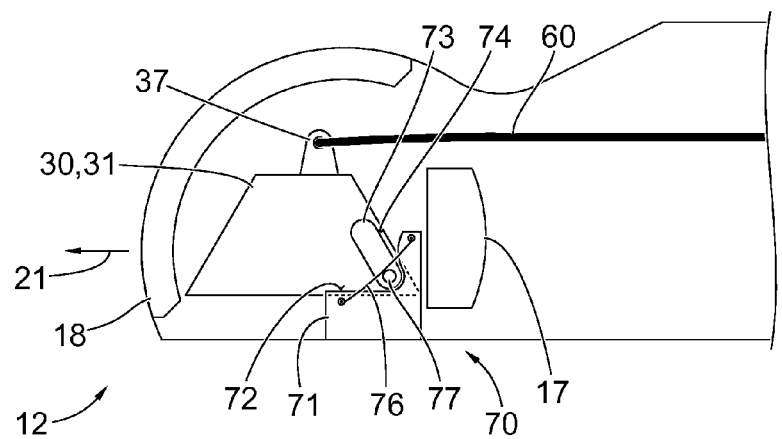
FIG. 10 shows a schematic depiction of an additional distal end of an endoscope.
Figure 11:
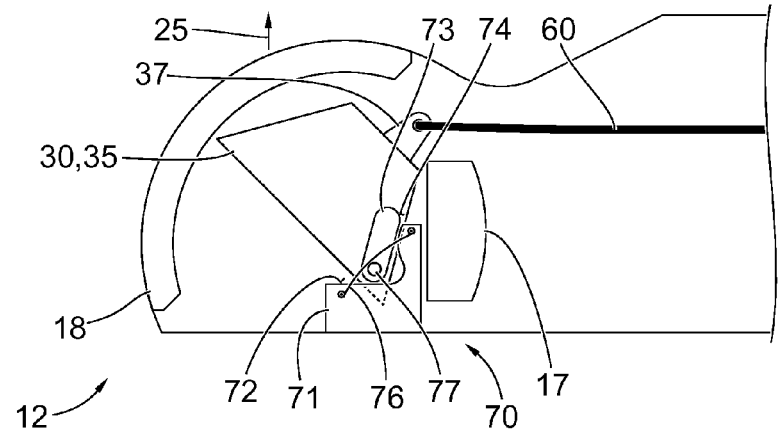
FIG. 11 shows another schematic depiction of the distal end from FIG. 10.

FIGS. 10 and 11 show schematic depictions of an additional embodiment of a distal end 12 of an endoscope, which resembles in some features the embodiments in FIGS. 2 through 6. In particular, a prism 30 is foreseen as light-diverting device between a window component 18 and a distal lens 17, which can be controlled or moved by means of a control wire 60.

Contrary to the embodiments in FIGS. 2 through 9, the prism 30 is not mounted over one or more diverters in the endoscope. Instead, a glide surface device 70 is foreseen. Said glide surface device 70 includes a fixed glide surface body 71 with a glide surface 72 and a glide surface body 73 on the prism 30 with a glide surface 74. The glide surface 72 on the fixed glide surface body 71 is essentially L-shaped. The glide surface body on the prism 30 is lengthwise or rod-shaped. In particular the end of the glide surface body 73 on the prism 30, facing the fixed glide surface body 71 is rounded. In addition the glide surface device 70 includes a flat spring 76 whose ends are mounted on the fixed glide surface body 71, and a pin 77 on the glide surface body 73 on the prism 30. The flat spring 76 is contiguous with the pin 77 and presses the glide surface 74 on the glide surface body on the prism 30 against the glide surface 72 on the fixed glide surface body 71.

The glide surfaces 72, 74, flat spring 76 and pin 77 are configured and disposed in such a way that the prism 30 assumes a well-defined predetermined position at every possible orientation. Thus the glide surface 74 on the glide surface body 73 on the prism 30 is contiguous with the glide surface 72 on the fixed glide surface body 71 in a connecting area (for example, the situation indicated in FIG. 10) or in two spatially separated areas (for example, the situation indicated in FIG. 8). Because of the shape and arrangement of the glide surface 72 on the fixed glide surface body 71 and the shape and arrangement of the glide surface 74 on the glide surface body 73 on the prism 30, the movement between a first position 31 of the prism 30 as shown in FIG. 1, which corresponds to the first viewing angle 21, and a third position 35, corresponding to the third viewing angle 25, can be adjusted or determined virtually without limits.

In each of the embodiments in FIGS. 2 through 8, a different light-diverting device can be foreseen each time instead of the prism 30, for example an object lens, a lens or a mirror. In particular when the light-diverting device is an object lens or includes an object lens, a light-sensitive image sensor can be rigidly coupled with the object lens. In addition, several light-diverting devices can be foreseen, which can execute different movements.

What is claimed is:

1. An endoscope with a viewing angle that can be adjusted within a predetermined angular range, comprising:
    a shaft with a distal end and a proximal end,
    a movable light-diverting device disposed within the distal end of the shaft, on whose orientation the viewing angle of the endoscope depends,
    a jointed device disposed within the distal end of the shaft, the jointed device connecting the light-diverting device with the shaft for movably holding the light-diverting device,
    such that the jointed device provides mobility of the light-diverting device within the shaft that includes more than only a capacity to pivot about a single pivot axis,
    the jointed device including a first joint that defines a first pivot axis and a second joint that defines a second pivot axis,
    the first joint being configured and disposed in order to allow a pivot movement of the light-diverting device about the first pivot axis if the viewing angle is situated in a first partial area of the predetermined angular range,
    the second joint being configured and disposed in order to allow a pivot movement of the light-diverting device about the second pivot axis if the viewing angle is situated in a second partial area of the predetermined angular range, and
    an elastic element, which is coupled with the jointed device in such a way that at least either the first joint is pre-tensed in a direction toward a first predetermined angular position or the second joint is pre-tensed in a direction toward a second predetermined angular position.

2. The endoscope according to claim 1, wherein the first partial area and the second partial area border on one another.

3. The endoscope according to claim 1, further comprising:
    a device to hamper a pivot movement about the second pivot axis, such that the hampering device is configured to hamper the pivot movement at least when the viewing angle is situated outside the second partial area.

4. The endoscope according to claim 1, further comprising:
    a device to block a pivot movement about the first pivot axis, such that said blocking device is configured to block the pivot movement about the first pivot axis if the viewing angle is not situated within the first partial area.

5. The endoscope according to claim 1, wherein the light-diverting device includes at least either a prism, an object lens, a lens, or a mirror.

6. The endoscope according to claim 1, further comprising a light-sensitive image sensor, the light-sensitive image sensor being coupled with the light-diverting device in such a way that the light-sensitive image sensor can move with the light-diverting device.

7. An endoscope with a viewing angle that can be adjusted within a predetermined angular range, comprising:
    a shaft with a distal end and a proximal end,
    a movable light-diverting device disposed within the distal end of the shaft, on whose orientation the viewing angle of the endoscope depends, and a jointed device disposed within the distal end of the shaft, the jointed device connecting the light-diverting device with the shaft for movably holding the light-diverting device, such that the jointed device provides mobility of the light-diverting device within the shaft that includes more than only a capacity to pivot about a single pivot axis, the jointed having a first joint that defines a first pivot axis and a second joint that defines a second pivot axis, wherein the jointed device includes a first diverter, which connects the first joint and the second joint, and a second diverter, which connects a third joint and a fourth joint, such that the second joint and the fourth joint are mechanically rigidly connected with the light-diverting device.

8. The endoscope according to claim 7, wherein the light-diverting device includes at least either a prism, an object lens, a lens, or a mirror.

9. The endoscope according to claim 7, further comprising a light-sensitive image sensor, the light-sensitive image sensor being coupled with the light-diverting device in such a way that the light-sensitive image sensor can move with the light-diverting device.

10. An endoscope with a viewing angle that can be adjusted within a predetermined angular range, comprising:

a shaft with a distal end and a proximal end, a movable light-diverting device disposed within the distal end of the shaft, on whose orientation the viewing angle of the endoscope depends, and a jointed device disposed within the distal end of the shaft, the jointed device connecting the light-diverting device with the shaft for movably holding the light-diverting device, such that the jointed device provides mobility of the light-diverting device within the shaft that includes more than only a capacity to pivot about a single pivot axis, wherein the jointed device includes a glide surface device for guidance along a path.

11. The endoscope according to claim 10, wherein the jointed device includes at least either a sliding block guide, a diverter, a cam control, or an elastic element.

12. The endoscope according to claim 10, wherein the light-diverting device includes at least either a prism, an object lens, a lens, or a mirror.

13. The endoscope according to claim 10, further comprising a light-sensitive image sensor, the light-sensitive image sensor being coupled with the light-diverting device in such a way that the light-sensitive image sensor can move with the light-diverting device.

* * * * *